United States Patent [19]

Kelln et al.

[11] Patent Number: 5,071,625
[45] Date of Patent: * Dec. 10, 1991

[54] CUVETTE HANDLING

[75] Inventors: Norman G. Kelln; Larry A. Nelson; Thomas O. Tiffany, all of Spokane, Wash.

[73] Assignee: Fisher Scientific Company, Pittsburgh, Pa.

[*] Notice: The portion of the term of this patent subsequent to Apr. 8, 2003 has been disclaimed.

[21] Appl. No.: 145,976

[22] Filed: Jan. 20, 1988

Related U.S. Application Data

[62] Division of Ser. No. 706,073, Feb. 27, 1985, Pat. No. 4,738,825.

[51] Int. Cl.$^5$ .................. G01N 1/10; G01N 21/07; G01N 35/00
[52] U.S. Cl. ........................... 422/72; 422/64; 422/102; 356/246
[58] Field of Search .............. 422/64, 65, 66, 67, 422/72, 73, 102, 258; 356/36, 246

[56] References Cited

U.S. PATENT DOCUMENTS

| | | | |
|---|---|---|---|
| Re. 29,880 | 1/1979 | Duff | 422/64 |
| 3,586,484 | 6/1971 | Anderson | 23/230 R |
| 3,759,666 | 9/1973 | Hill | 23/230 B |
| 3,798,459 | 3/1974 | Anderson | 250/218 |
| 3,813,031 | 5/1974 | Anderson | 356/36 |
| 3,829,223 | 8/1974 | Hamel | 356/246 |
| 3,873,217 | 3/1975 | Anderson | 356/246 |
| 3,909,201 | 9/1975 | Matte | 422/65 |
| 4,123,173 | 10/1978 | Bullock | 356/246 |
| 4,226,531 | 10/1980 | Tiffany | 422/258 |
| 4,314,970 | 2/1982 | Stein | 422/72 |
| 4,373,812 | 2/1983 | Stein | 422/72 |
| 4,456,581 | 6/1984 | Edelmann | 422/72 |
| 4,580,897 | 4/1986 | Nelson | 422/64 |
| 4,580,898 | 4/1986 | Keramaty | 422/64 |
| 4,708,886 | 11/1987 | Nelson | 422/72 |

FOREIGN PATENT DOCUMENTS 3246274 6/1983 Fed. Rep. of Germany .

Primary Examiner—David L. Lacey
Assistant Examiner—Kimberly A. Trautman
Attorney, Agent, or Firm—Fish & Richardson

[57] ABSTRACT

An analysis system of the concurrent type has a multicuvette unit supply station, a loading station, an analysis station, and transport mechanism for transporting cuvette units in correlated orientation between the several stations. Each cuvette unit includes mechanical interlock structure that cooperates with orientation structure at each of the several stations and with orientation structure carried by the transport mechanism so that continuity of cuvette orientation information is maintained throughout loading and concurrent analysis of the several samples in the cuvette unit.

10 Claims, 9 Drawing Sheets

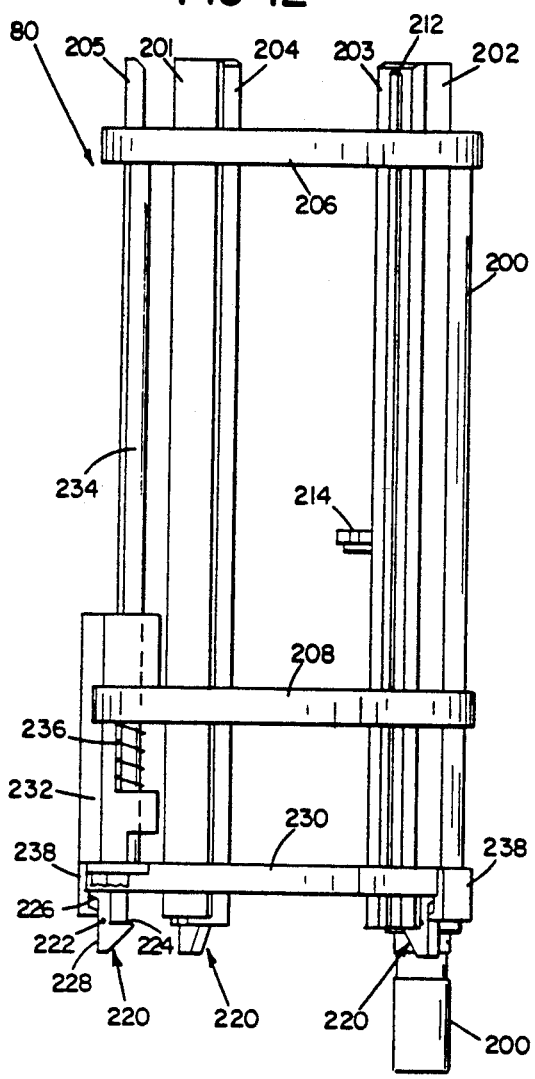
FIG 12
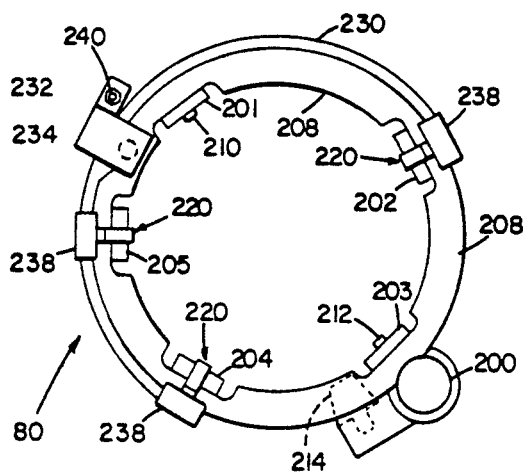
FIG 13
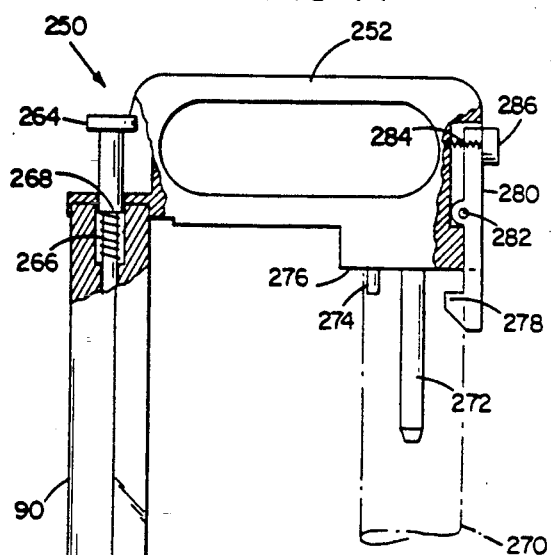
FIG 14
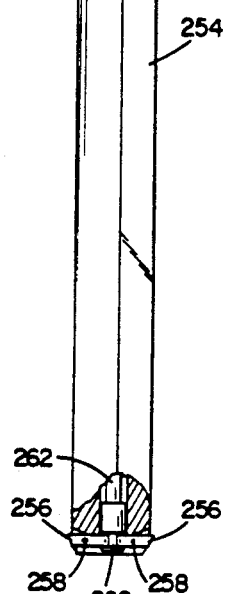
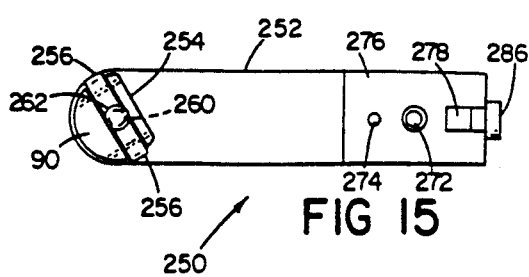
FIG 15

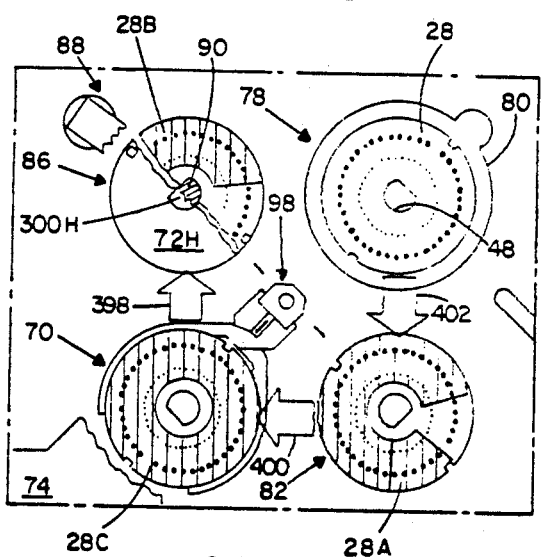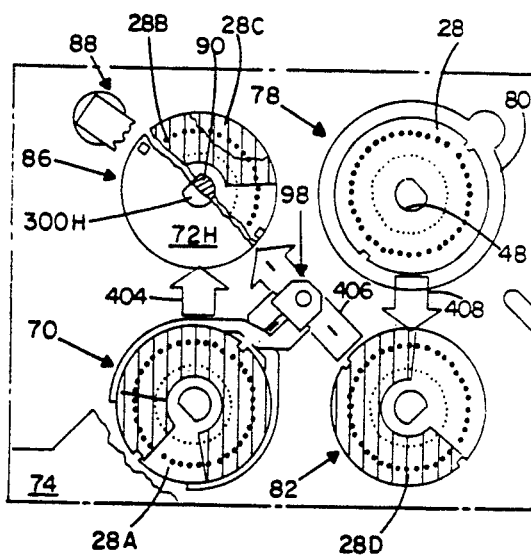

CUVETTE HANDLING

This is a divisional of application Ser. No. 706,073, filed Feb. 27, 1985 now U.S. Pat. No. 4,738,825.

This invention relates to analysis systems, and to systems for the concurrent analyses of a plurality of fluid samples, and has particular application to apparatus for the analysis of constituents of biological fluids such as blood.

While many chemical instruments are of the continuous or discard type and perform analyses sequentially, other known analyzer instruments perform analyses concurrently with the use of multicuvette analysis units. Such concurrent analyzers perform measurements rapidly, accurately and inexpensively; and are in extensive use in laboratories. An example of such an analyzer is a clinical analyzer of the centrifugal type which uses a multicuvette rotor unit that has a plurality of spaced elongated radially extending plural chamber cuvettes arranged in circumferential array. Each cuvette has a first chamber for initially holding a first reactant (frequently a sample of blood or other biological fluid), and a second chamber for initially holding one or more different reactants. After cuvettes of the rotor are loaded with samples to be analyzed and reagents in a loading system, the rotor is transferred to an analysis system where the rotor is spun and the reactants are transferred by centrifugal force to analysis regions at the outer ends of the several rotor cuvettes for mixing, reaction and subsequent analysis by photometric or other appropriate analysis technique.

Clinical analyzers are useful in performing a variety of analyses, including kinetic and endpoint analyses, by techniques such as absorption, light scattering, and/or fluorescence. In such analyses, accurate identification of each sample and the particular analysis to be performed must be maintained throughout the analysis sequence. Such identification is relatively easy in analyzers of the sequential type, while the maintaining of accurate identification of the several analyses that are being performed concurrently with a common multicuvette unit in analyzers of the concurrent type is more complex.

In accordance with one aspect of the invention, there is provided an analysis system of the concurrent type which has a multicuvette unit supply station, a loading station, an analysis station, and transport mechanism for transporting cuvette units in correlated orientation between the several stations. Each cuvette unit includes mechanical interlock structure that cooperates with orientation structure at each of the several stations and with orientation structure carried by the transport mechanism so that continuity of cuvette orientation information is maintained throughout loading and concurrent analysis of the several samples in the cuvette unit.

In accordance with another aspect of the invention, there is provided an analysis system with an analysis compartment that preferably is maintained at a controlled and stabilized temperature at which the analyses are to be performed. A plurality of multicuvette units of long thermal time constant material are stored in the compartment adjacent a supply station and a transport mechanism in the compartment is adapted to transport cuvette units sequentially from the supply station to a loading station also in the compartment where a transfer mechanism is arranged for loading predetermined quantities of sample and reagent into a plurality of the cuvettes in the unit. An analysis station and a cuvette hold station are also in the compartment, and the transport mechanism moves loaded cuvette units selectively to the analysis and hold stations in an arrangement that provides analysis results rapidly and with versatility, the numerous different available analysis procedures being organized by the system controller according to factors such as urgency of request and efficiency of system operation.

In a particular embodiment, the analyzer system is of the centrifugal analyzer type and uses multicuvette rotor units that have each a plurality of spaced elongated radially extending plural chamber cuvettes arranged in circumferential array. Orientation structure on each rotor includes peripheral interlock structure, central interlock structure, and intermediate interlock structure in the form of a recess in the body of the rotor. The rotors are disposed at the supply station in the analytical compartment in stacked relation in feeder tower structure which has orienting structure extending along the tower to maintain the stack of rotors in angularly aligned relation. At each of the loading, holding and analysis station, rotor support table structure includes an aligning hub and an auxiliary projection on the table support surface which cooperates with the rotor recess to establish rotor alignment with the rotor at that station. The rotor tables at the loading and analysis stations carry angular position indicia (in the form of timing slot structure) which cooperates with sensor structure to provide rotor cuvette information to the system control. The rotor drive at the loading station includes a stepping motor indexing mechanism for sequentially positioning cuvettes at the loading station for receipt of sample and reagent materials for analysis while the rotor drive at the analysis station includes a DC motor for driving the rotor at a mixing and analysis speeds, rotor braking structure, and stepper motor structure which is clutch coupled to the drive for positioning the rotor in desired angular orientation.

The transport mechanism includes a rotor support mechanism in the form of a pair of gripping arms that are arranged effectively to grasp the periphery of the rotor for transport between stations, together with an alignment member that engages peripheral rotor orientation structure to maintain the rotor in angular alignment during transport between stations. While the alignment mechanisms may take a variety of forms, in a particular embodiment the alignment mechanism carried by the transport mechanism is a projecting member which engages a notch in the flange of the rotor. Rotor flange notches are also utilized for aligning the rotors in the feeder tower, two substantially opposed rotor flange notches engaging rails in the feeder tower so that the angular rotor alignment is maintained as the rotors are fed sequentially from the tower. The feeder mechanism includes a mechanical release mechanism that is operated by the transport mechanism for feeding one rotor at a time from the supply tower. Actuator mechanism at each of the loading, holding and analysis stations operates the gripping arms of the transport mechanism to grasp and release rotors in the sequence of depositing rotors at the respective stations or moving them from that station to another station.

The analysis system maintains and retains accurate information on sample identification and reagent materials throughout the loading and analyses cycles, including identification of the particular cuvette and the rotor that is used in each analysis. The indexing and alignment portions of each rotor cooperate with rotor orientation structure on the transport mechanism and at each of the stations to provide the coordinated handling of the rotors in an automated centrifugal analyzer system that operates under system control.

Other features and advantages of the invention will be seen as the following description of a particular embodiment progresses, in conjunction with the drawings, in which.

Figure 1:
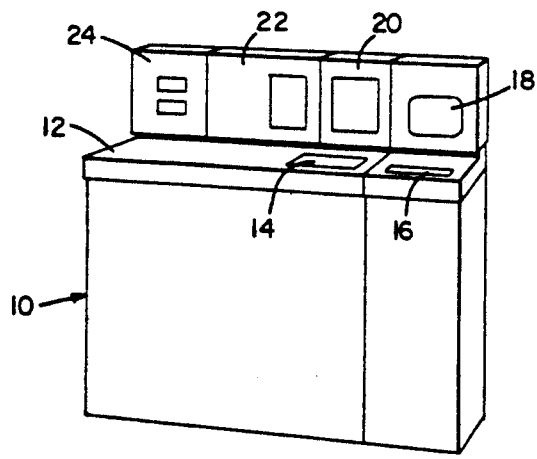
FIG. 1 is a perspective view of a centrifugal analyzer system in accordance with the invention.
Figure 3:
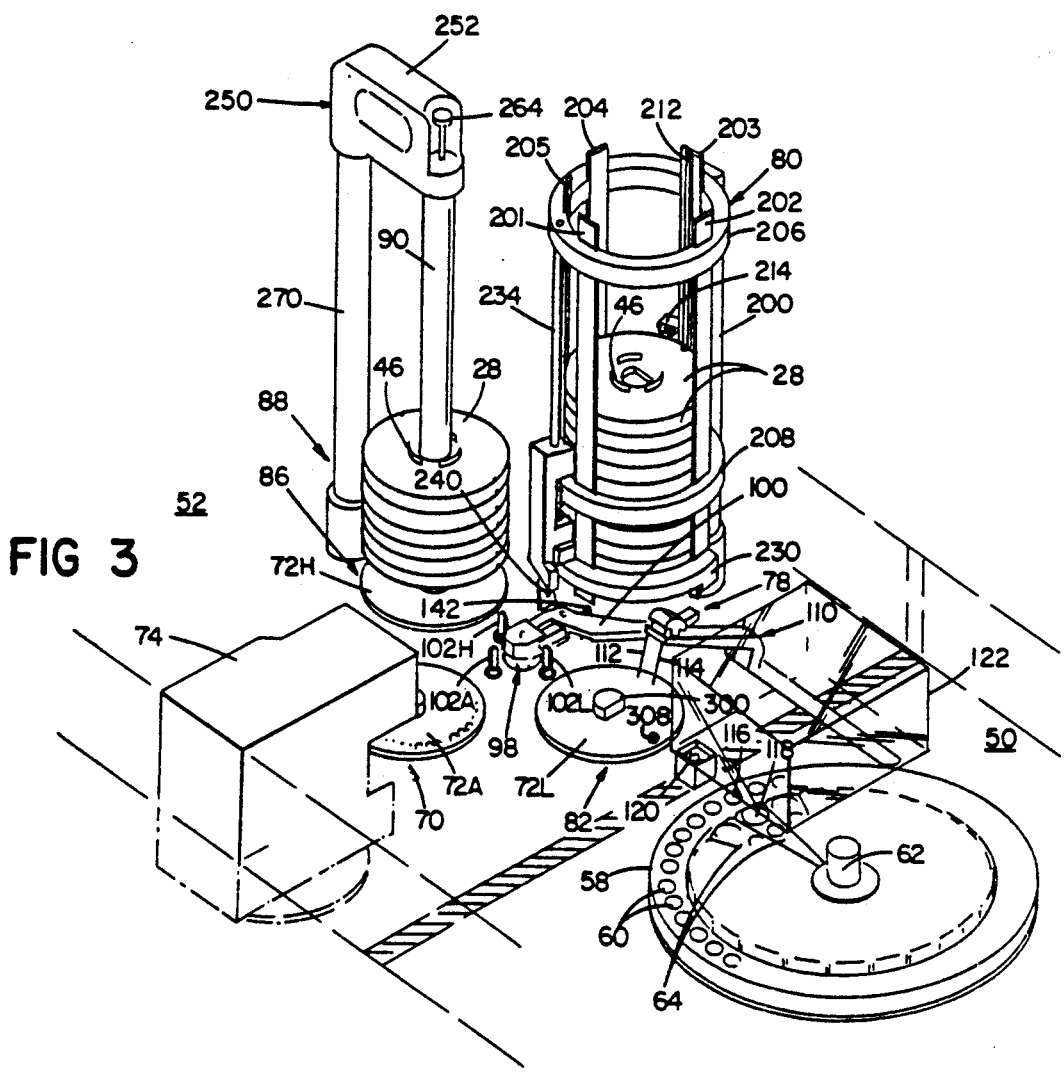
FIG. 3 is a perspective view of components of the analyzer system of FIG. 1.
Figure 4:
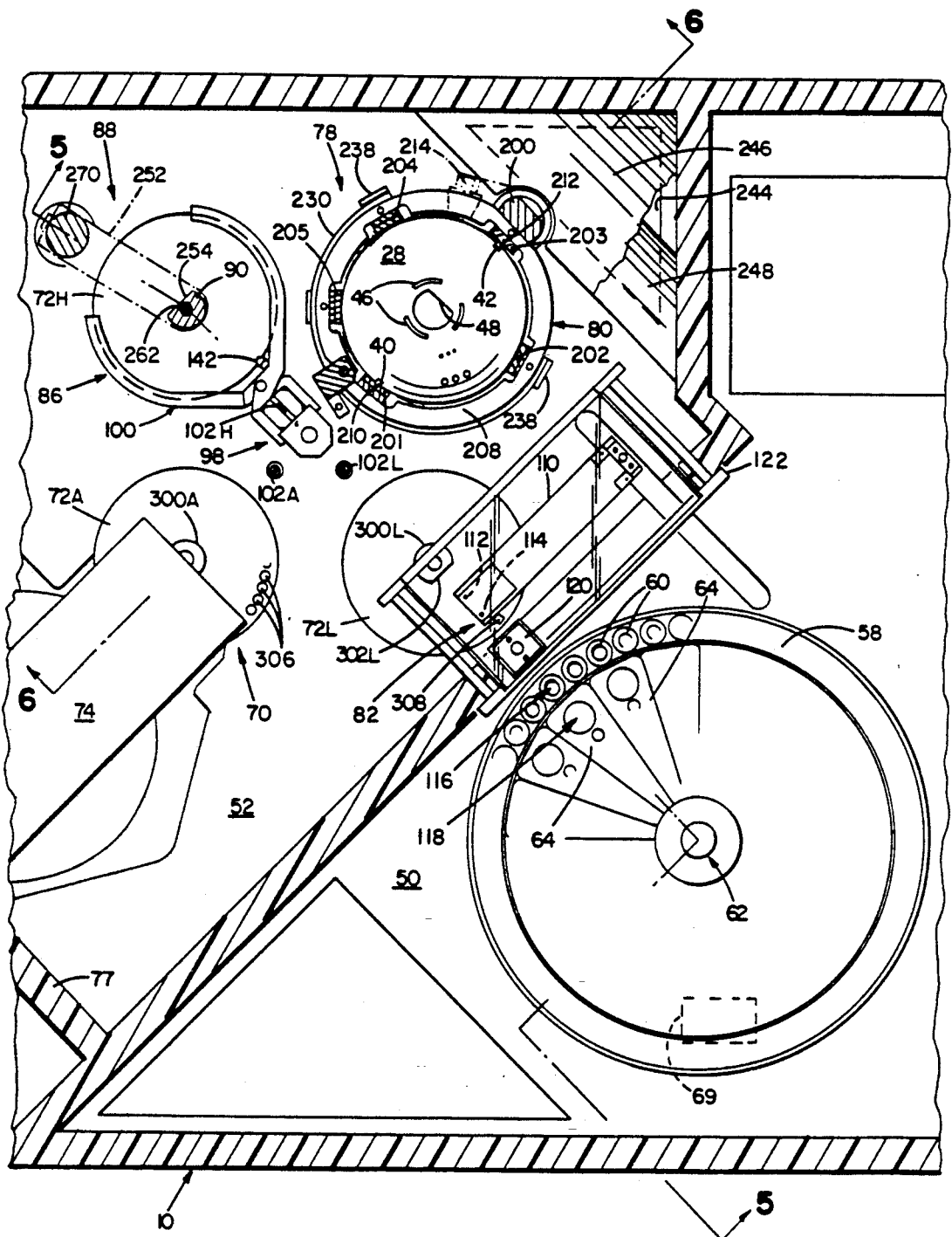
Figure 5:
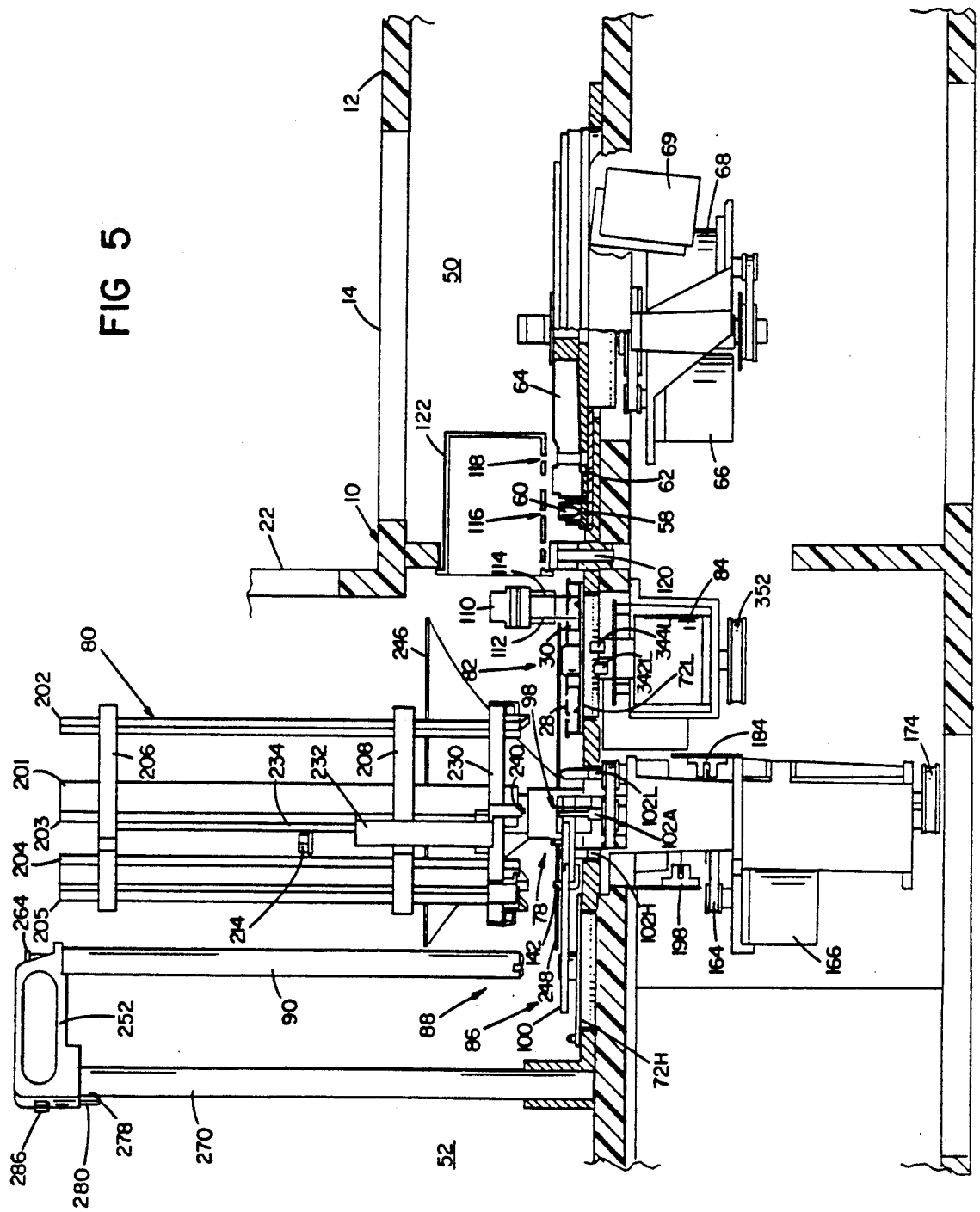
Figure 6:
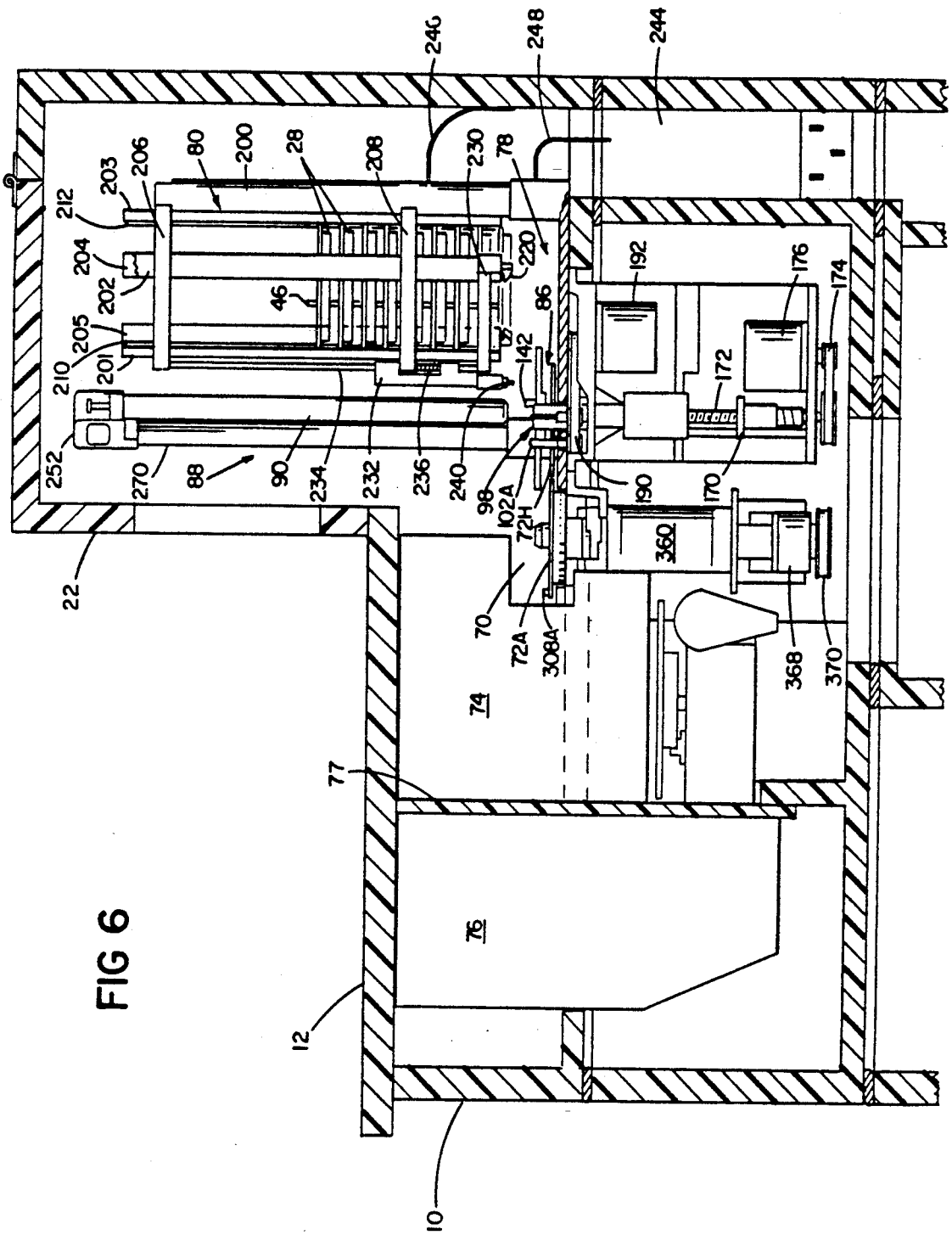
Figure 7:
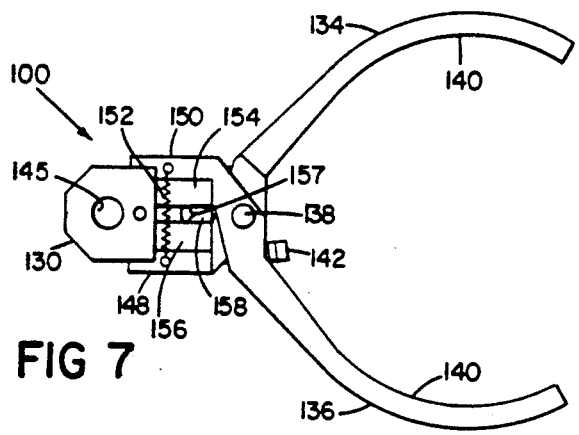
Figure 8:
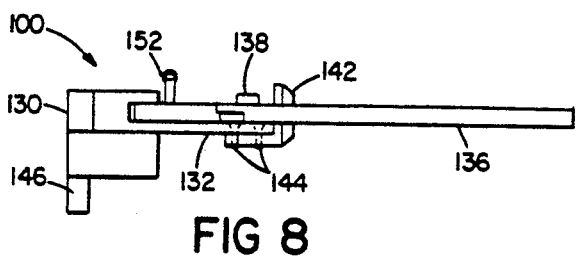
Figure 9:
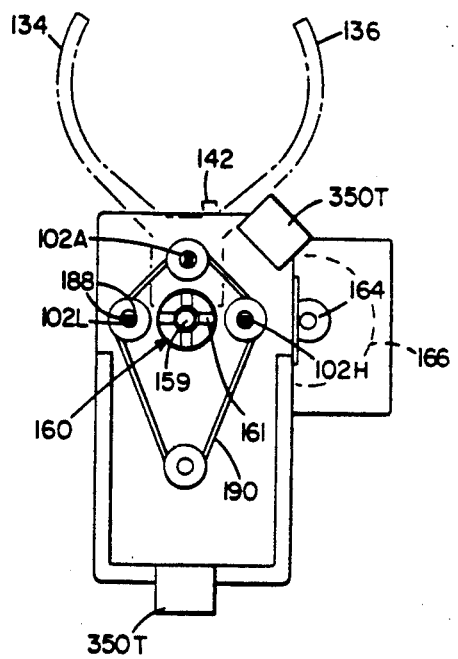
Figure 10:
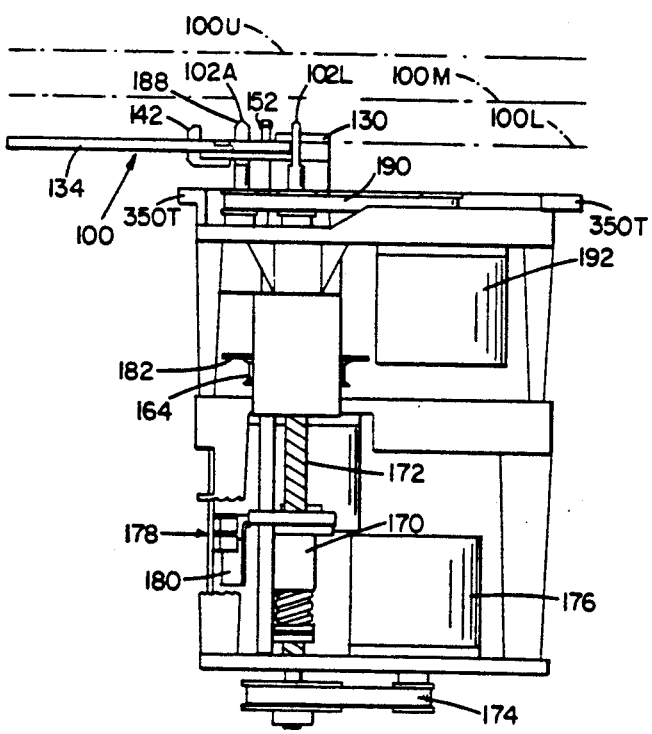
Figure 11:
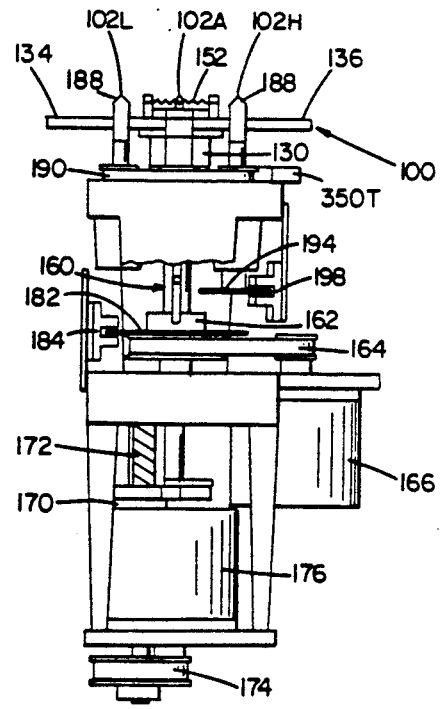
Figure 16:
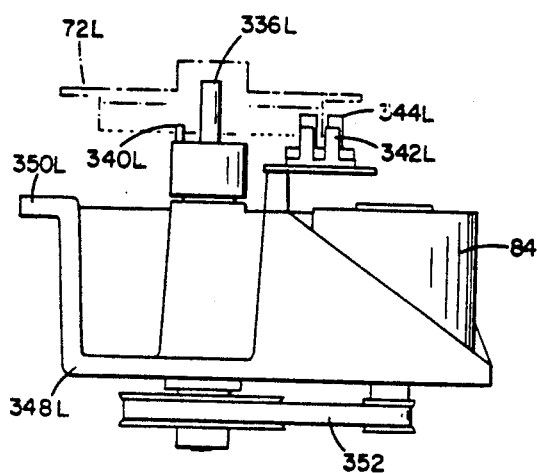
Figure 20:
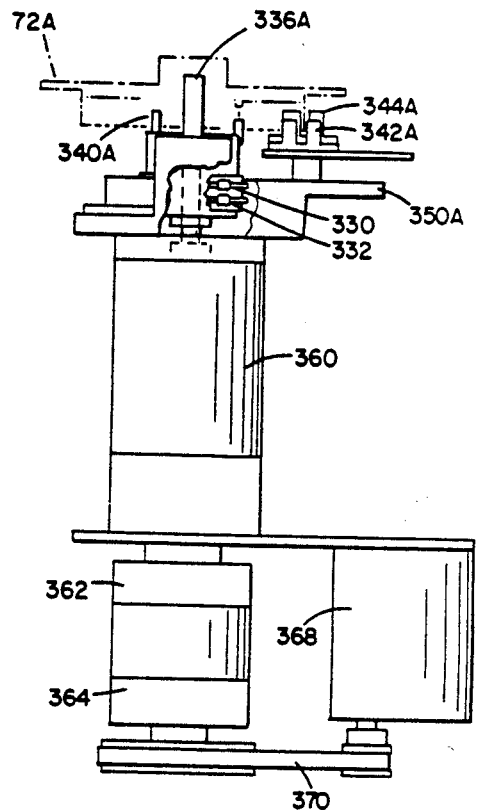
Figure 17:
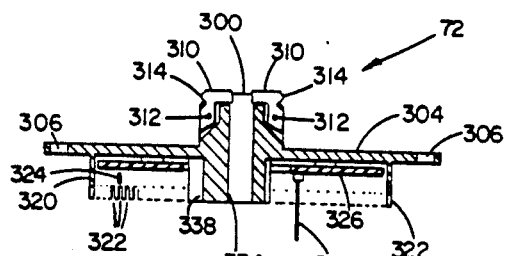
Figure 18:
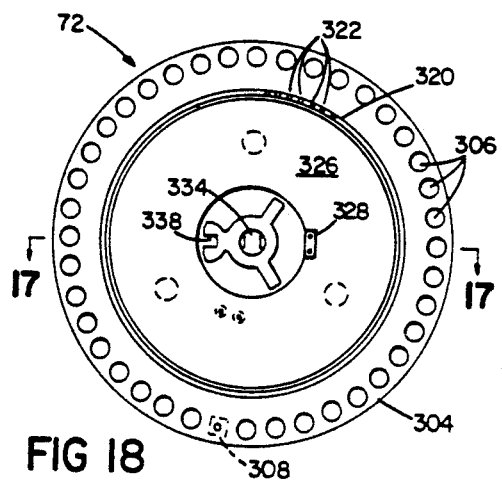
Figure 19:
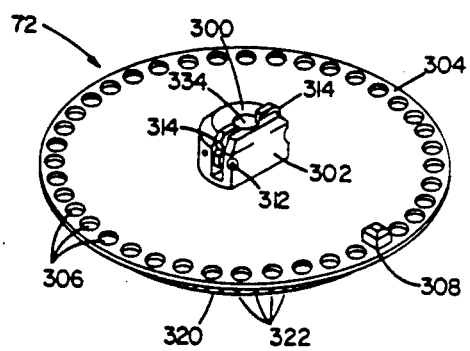

FIG. 4 is top plan view of components of the analyzer system shown in FIG. 3 (with a rotor 28 at loading station 82 and isolation chamber moved into compartment 52);

FIG. 5 is a sectional view taken along the line 5—5 of FIG. 4;

FIG. 6 is a sectional view taken along the line 6—6 of FIG. 4;

FIG. 7 is a top plan view of a rotor handling mechanism used in the system of FIG. 1;

FIG. 8 is a side view of the mechanism shown in FIG. 7;

FIG. 9 is a top plan view of rotor transport mechanism employed in the analyzer system shown in FIG. 1;

FIG. 10 is a side elevational view of the rotor transport mechanism of FIG. 9;

FIG. 11 is a front elevational view of the rotor transport mechanism of FIG. 9;

FIG. 12 is a side elevational view of rotor feed tower structure used in the system of FIG. 1;

FIG. 13 is a bottom view of the feed tower structure shown in FIG. 12;

FIG. 14 is a side elevational view of a rotor handling implement used in the system of FIG. 1;

FIG. 15 is a bottom view of the implement shown in FIG. 14;

FIG. 16 is a side elevational view of rotor support table indexing structure at the loading station of the analyzer system shown in FIG. 1;

FIG. 17 is a sectional view of the analyzer station rotor drive table used in the system of FIG. 1 taken along the line 17—17 of FIG. 18;

FIG. 18 is a bottom view of the drive table shown in FIG. 17;

FIG. 19 is a perspective view of the analyzer station rotor drive table;

FIG. 20 is a side elevational view of table drive structure at the analyzer station of the analyzer system shown in FIG. 1; and FIGS. 21A-H are a series of diagrammatic views showing an illustrative operational sequence of the analyzer system.

DESCRIPTION OF PARTICULAR EMBODIMENT

The analysis system shown in FIG. 1 is of the centrifugal analyzer type and includes base unit 10 with top deck 12 in which is disposed door 14 for access to the supply/reagent compartment and operator input control keyboard 16; and back panel unit with output display 18, hinged panel 20 for access to metering pumps, hinged panel 22 for access to rotor feed tower and rotor discard stack mechanisms, and disc drive panel 24.

Figure 2:
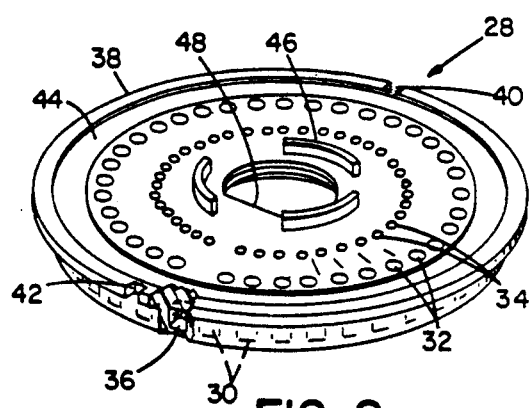
FIG. 2 is a perspective view of an analyzer rotor used in the system of FIG. 1.

The rotor assembly 28 employed in this analyzer is shown in FIG. 2 and has a diameter of about ten centimeters, an overall body height of about one centimeter and is formed of ultraviolet transmitting material that has appropriate transparency, chemical resistance and optical characteristics for photometric analysis. Rotor assembly 28 defines a circumferential array of thirty-nine individual analysis cuvettes 30 (each of which has corresponding loading ports 32, 34) and a reference region that includes orienting interlock structure in the form of socket recess 36. Rotor 28 has circumferential flange structure 38 with interlock structure in the form of alignment notches 40, 42; optical window channel 44 disposed inwardly of flange 38; and a series of three arcuate spacer ribs or standoffs 46 (about one quarter centimeter high) that are disposed about interlock structure in the form of central D-shaped aligning aperture 48. Further details of rotor 28 may be had with reference to co-pending application Ser. No. 615,501 filed May 31, 1984 entitled Centrifugal Analyzer Rotors, now U.S. Pat. No. 4,580,897, the disclosure of which is incorporated herein by reference.

With reference to FIGS. 3–6, disposed within base housing 10 is thermally isolated storage compartment 50 and thermally isolated analysis compartment 52. Further details of compartments 50, 52 may be had with reference to co-pending application Ser. No. 706,072 filed concurrently herewith entitled ANALYSIS SYSTEM now U.S. Pat. No. 4,208,886 the disclosure of which is incorporated herein by reference. Access to sample/reagent compartment 50 is through sliding door 14 on the deck 12 of base 10, an interlock switch being used to detect open and closed positions of the door 14 which must remain closed during rotor loading and analysis. Disposed in sample/reagent compartment 50 is a forty-four place sample ring 58 that holds sample containers 60 and a twenty place reagent tray 62 that holds reagent containers 64 of the type shown in co-pending application Ser. No. 706,074 filed concurrently herewith entitled REAGENT HANDLING, now U.S. Pat. No. 4,764,342, the disclosure of which is also incorporated herein by reference. Sample ring 58 is rotated by stepper motor 66 while reagent tray 62 is rotated by stepper motor 68 (FIG. 5). An optical barcode reader 69 is used to read barcodes on reagent containers 64.

Disposed in analysis compartment 52 is an analysis station 70 that includes rotor support table 72A and cooperating optics module 74. A rotor 28 on support table 72A is driven in rotation to mix sample and reagent materials in each of several cuvettes of the rotor and then to analyze the resulting chemical reactions through use of light sources housed in compartment 76 (that is isolated from compartment 52 by thermal isolation wall 77—FIGS. 4 and 6) by absorbance or fluorescence/light scatter techniques.

Also disposed in analysis compartment 52 is supply station 78 that has rotor feed tower 80; loading station 82 that has rotor support table 72L indexed by stepping motor 84 (FIG. 5); auxiliary (holding/incubation) station 86 that has rotor support table 72H; and discard station 88 that includes storage post 90 which receives used rotors and is vertically above and aligned with hub 300H of support table 72H. Rotor transport mechanism 98 includes articulated rotor transport arm assembly 100, and three actuator members in the form of double flatted cam members 102 which cooperate with arm assembly 100 to grasp and release rotors 28 and to transport rotors between stations 78, 82, 70, 86 and 88.

A liquid transfer mechanism 110 of the type shown in co-pending application Ser. No. 706,070 filed concurrently herewith entitled LIQUID HANDLING, now U.S. Pat. No. 4,670,210 the disclosure of which is also incorporated herein by reference includes two stainless steel pipette tubes 112, 114 that are moved between a reagent container 64 at reagent loading station 118, a sample container 60 at sample loading station 116, wash bath 120 and a rotor cuvette 30 at loading station 82. A particular sample and one or more reagents are specified by the system controller for each analysis and appropriate sample and reagent containers are positioned at stations 116, 118 by indexing mechanisms 66 and 68. When access door 14 is opened, isolation chamber 122 is retracted into analysis compartment 52 (as shown in FIG. 4) to allow access to sample ring 58 and reagent tray 62. During loading, transfer arm 110 moves (via isolation chamber 122 that has been moved into storage compartment 50 as shown in FIG. 5 so that arm 110 is in thermal communication with chamber 52 but essentially thermally isolated from chamber 50) into the region of sample/reagent compartment 50 to draw up sample and reagent liquids from the sample and reagent containers 60, 64 at stations 116, 118 respectively and then transport those liquid quantities to a rotor 28 at loading station 82 for dispensing of precise quantities of sample and reagent through ports 32, 34 into the cuvette 30 positioned at loading station 82 (FIG. 5). After loading, rotor 28 is moved to analysis station 70 where the rotor is spun and its contents analyzed. As indicated above, it is imperative that the analysis system maintain and retain accurate information on sample identification and reagent materials throughout the loading and analysis including identification of the particular cuvette 30 and the rotor 28 that is used in each analysis. Each rotor 28 has interlock and alignment portions in the form of flange notches 40, 42, socket 36 and D-shaped central opening 48. Transport assembly has cooperating rotor orienting member 142; tables 72 include cooperating orienting hubs 300 and posts 308; and rotatable tables 58, 62, 72A and 72L also include angular position indicators on annular skirts 320 that interface with optical sensors.

Rotor transport mechanism 98 is an electromechanical device for automated handling of rotors 28 within the analysis compartment 52 and includes arm assembly 100 that is moved vertically between three specific heights 100U, 100M and 100L (FIG. 10) with capability (at level 100M) of 360° of rotational motion between four specific stop points—at supply station 78, loading station 82, analysis station 70, and park-discard station 86, 88—and arm actuation capability by cams 102 at three of those four rotational stop points. Further details of the transport mechanism may be seen with reference to FIGS. 7-11. Arm assembly 100, as shown in FIGS. 7 and 8, includes body 130 that has projecting support plate 132 on which two curved caliper arms 134, 136 are secured for scissoring movement about the axis of bolt 138. The curved arms 134, 136 define an area for receiving a rotor 28 with rotor flange 38 resting on their upper surfaces and inner arm surfaces 140 gripping the rotor body. Rotor aligning member 142 is secured to plate 132 by fasteners 144 and projects from arm 136 so that it enters flange notch 40 to orient the rotor 28 in the transport arm assembly 100. Passage 145 through body 130 receives upstanding alignment shaft 159 of drive assembly 160, and depending drive projection 146 is received in a drive slot 161 of drive assembly 160. Spring 152 is coupled between rearward arm extensions 148, 150 of caliper arms 134, 136 and biases arms 134, 136 in closing action towards one another against the stops carried by body 130—the position shown in FIG. 7. Bushing elements 154, 156 carried by arm extensions 148, 150 respectively have spaced opposed surfaces 157 which define opening 158 for receiving a cam actuator 102.

With reference to FIGS. 9-11 rotor transport assembly 100 is secured on shaft assembly 160 that is driven in rotation through coupling 162, belt drive 164 and stepper motor 166; and driven vertically through coupling 170, lead screw 172, 3:1 reduction belt drive 174 and stepper motor 176. Lead screw 172 has a one inch lead such that each step of motor 176 produces about 0.05 millimeter of vertical movement of shaft assembly 160. Vertical motion sensor assembly 178 monitors the position of shutter 180 to provide outputs indicative of upper arm assembly position 100U, mid arm assembly position 100M, and lower arm assembly position 100L. Disc 182 is carried by shaft assembly 160 and has eight timing slots and one "home" hole that are monitored by optical sensors 184. The three cam members 102L, 102A and 102H are coordinately driven by belt drive 190 and stepper motor 192 and their position is monitored by disc 194 and optical sensor 198.

Rotational movement of the transport assembly 100 is permitted only at the midlevel 100M as indicated by sensors 178 and vertical movement of assembly 100 is permitted only when the assembly is at a station (as indicated by sensors 184). When the transport assembly 100 is at a station, the assembly may be moved between vertical levels U, M and L as monitored by sensors 178. At supply station 78, motor 176 raises the transport assembly to level 100U to release a rotor 28 from feeder tower 80 with the rotor being aligned by the interengagement of flange notch 40 and projection 142. At the loading station 82, the transport assembly 100 is lowered to position 100L by motor 176 with the flatted cam 102L entering slot 158 between bushings 154, 156. The double flatted cams 102 are then rotated 90° by motor 192 to spread the arms 134, 136 and release the rotor 28 carried by the arms for deposit on loading table 84 as aligned by D-shaped table hub 300 and alignment post 308. Motor 176 then raises the transport mechanism 100, and as the open arms 134, 136 clear the actuator cam 102L they are closed by spring 152. Motor 192 then returns the cams 102 to their original position. When transport mechanism 98 is to pick up a rotor 28 from loading station 82, the actuator cams 102 are first rotated to their arm open position (as sensed by sensor 198) and as the arm assembly 100 is lowered by motor 176, their inclined surfaces 188 cam the arms 134, 136 open so that they pass the flange 38 of the rotor 28 on table 72L, and then motor 192 rotates the actuator cams 102 to their arm closed positions so that the arms 134, 136 clasp the rotor body for lifting that rotor to the intermediate level 100M and transport to either the analysis or park station table 72 where the rotor 28 is deposited. Mechanism 78 similarly picks up rotors 28 at stations 70 and 86.

Further details of feeder tower 80 may be seen with reference to FIGS. 4, 5, 12 and 13. That rotor feeder tower 80 includes support post 200 and vertical bar members 201-205 to which ring members 206 and 208 are bolted to provide a cage assembly. Bar members 201 and 203 carry rotor orienting key members 210, 212 which receive notches 40, 42 in the flanges 38 of rotors 28 to provide alignment of the rotors as stacked within tower 80. Tower 80 has a capacity of twenty-four rotors 28 and reflective sensor 214 (supported from post 200) provides an output to display 18 when there are less than nine rotors in the feeder tower to indicate that the tower should be recharged with additional rotors. Standoffs 46 space the rotors 28 from one another in the stack in feeder tower 80 so that the flow of heated air through passage 244 (FIG. 6) that is directed through the stack of rotors 28 and across stations 70, 82 and 86 by baffles 246, 248 thermally equilibrates the rotors to the analysis temperature.

Each vertical bar member 202, 204 and 205 carries a rotor stack support pawl mechanism 220 at its lower end. Each pawl mechanism, as shown in FIG. 12, is mounted on its bar member by pin 222 for pivoting movement and has a horizontal rotor support surface 224 on its inner side (on which the flange 38 of the lower most rotor 28 in the stack rests) and an inclined cam surface 226 and a vertical cam surface 228 on its outer side.

Actuator ring 230, at the base of tower 80, is mounted for vertical movement along bars 201–205 and is connected to slider member 232 that is mounted for sliding movement along vertical shaft 234 and that is biased towards a lower position (limited by fixed cage ring 208) by spring 236. C-ring 230 carries three actuator members 238 which engage pawl cam surfaces 226 when ring 230 is moved upward and rotate the lower portions 224 of those pawls outwardly in a rotor releasing action. Extending downwardly from the lower end of slider member 232 as may be seen in FIGS. 3, 5 and 6 is projection 240 which is engaged by transport mechanism body 130 when that transport mechanism 98 is at supply station 78 and is raised to its upper position 100U. That upward movement of the transport mechanism engages projection 240 and drives actuator ring 230 upward, camming the support surfaces 224 of pawls 220 outwardly, thereby releasing the bottom most rotor 28 in the tower 80 for deposit on the transport arms 134, 136 and support by rotor flange 38 with flange notch 40 being cammed into aligning member 142. Downward motion of the transport mechanism 100 then allows ring 230 to move down and close and lock the support pawls 220 so that surfaces 224 engage the flange 38 of the next rotor and support the stack of rotors 28 while the transferred rotor is carried by the transport arms 134, 136. When the rotor transport mechanism reaches its midposition 100M, motor 166 rotates the mechanism 100 to loading station 82.

Rotors 28 may be loaded into feeder tower 80 by the tool 250 shown in FIGS. 14 and 15. That tool includes handle portion 252 from which rotor orienting and support post 90 depends. Post 90 is of D-shaped cross-section with a flat surface 254 as indicated in FIG. 15 that conforms to the D-shape of rotor aperture 48. Thus post 90 maintains alignment of a stack of rotors loaded onto tool 250. Two latch pawls 256 are mounted on pivot pins 258 in slots 259 at the bottom of post 90. The inner ends of pawls 256 are received in recess 260 of actuator shaft 262 that passes through post 90. Shaft 262 is biased upwardly by spring 266 that acts against head portion 268 and has push button portion 264 at its upper end adjacent handle 252. Depression of push button 264 moves shaft 262 downwardly, rotating the tips of latch pawls 256 upwardly to release rotors 28 on post 90. A stack of new rotors may be carried on post 90 and inserted into feeder tower 80 with tool 250, push button 264 being depressed to release the stack of rotors after tool 250 has been inserted into tower 80 so that the rotors 28 are supported on surfaces 224 of support pawls 220.

Tool 250 is also used at discard station 88 as indicated in FIGS. 3–6 for receiving used rotors. The top of support post 270 (FIG. 5) at used rotor station 88, has recesses into which posts 272, 274 that depend from handle 252 of the tool 250 are received so that tool surface 276 is seated on top of post 270 with latch 278 engaged in a recess at the top of post 270. Latch lever 280 is mounted for pivoting movement about shaft 282 and is biased to latch position by spring 284. Depression of push button 286 releases latch 278 and allows the rotor handling tool 250 to be lifted from support post 270 by handle 252. When a used rotor 28 is to be loaded onto post 90, transport mechanism 98 moves to the discard station 88 immediately above and in alignment with hold table 72H so that aperture 48 of the rotor 28 held by caliper arms 134, 136 is aligned with the D-shaped post 90. Movement of mechanism 98 upwardly causes latch pawls 256 to pivot as rotor aperture 48 moves upwardly past pawls 256, and after the rotor aperture 48 has passed pawls 256 they return to the position shown in FIG. 14 and support the rotor on post 90. Transport mechanism 98 then moves downwardly to the midposition 100M and motor 166 rotates the transport mechanism to the next position as commanded by the analyzer control.

Details of the rotor support tables 72 may be seen with reference to FIGS. 16–20, the rotor support tables at loading station 82, analysis station 70 and park (hold) station 88 being similar. Each table 72 includes a D-shaped orienting hub 300 that has a flat surface 302 corresponding to the shape of central apertures 48 of rotors 28 and an orienting projection 308. The circumferential support surface 304 of analyzer table 72A has a series of thirty-nine apertures 306 around its periphery which are used during analysis at station 70, those apertures being aligned with projection 308 which cooperates with socket recess 36 in the base of the rotor body at the reference region. Carried by hub 300 are centrifugally actuated latch dogs 310 which are rotatably supported on pins 312 so that latch surfaces 314 spread radially outwardly during rotation of table 72A to hold the rotor 28 firmly in place. The thirty-nine holes 306 at the edge of the analysis table 72A allow light to pass through the bottoms of the rotor cuvettes 30 to a photomultiplier tube below analysis compartment 52 which provides analysis output signals. Annular depending skirt 320 has a series of eighty timing slots 322 and an index hole 324. A temperature sensor may be mounted within projection 308 and coupled via circuit board 326 and leads 328 to slip rings 330, 332 at analysis station 70 (FIG. 20).

Pilot shaft 336 is received in bore 334 in hub 300 and socket 338 receives drive stub 340 of the drive module at loading station 80 (FIG. 16) and at analysis station 70 (FIG. 20). At each of stations 70 and 80, timing slots 322 are disposed to be sensed by sensor 342 and index hole 324 is disposed to be sensed by sensor 344. Signals from sensors 342, 344 to the system controller provide on a continuous basis information on the angular position of rotor 28 on table 72, and thus identify individual cuvettes 30 being loaded or analyzed.

With reference to FIG. 16, the drive module at loading station 86 includes a support table 72L of the type shown in FIGS. 17-19, support frame 348 with mounting flanges 350 (similar to the other motor modules), drive motor 84 (12 volt 1.8° stepping motor that is driven in half step mode) that is coupled by 4:1 belt drive 352 to drive shaft 336L so that table 72L is indexed about 0.225° per step, forty steps of motor 84 incrementing table 72L one cuvette.

With reference to FIG. 20, analysis station 70 includes a support table 72A of the type shown in FIGS. 17-19. DC motor 360 drives shaft 336A at high speed for mixing and at a constant speed for analysis; braking action is provided by 24 volt DC brake 362 that generates fifteen inch pounds of braking torque, and clutch 364 connects the analysis station drive shaft 336A to stepping motor 368 via belt drive 370. Table 72A is indexed to appropriate orientation by motor 368 and a loaded rotor 28 is placed on the table by transport mechanism 98. With stepper motor 368 decoupled from drive shaft 336A, DC motor 360 is accelerated to approximately thirty-six hundred rpm and then the table is rapidly braked by brake 362 to mix the contents of the analysis cuvettes 30. After mixing, the rotor 28 is driven at approximately six hundred rpm by DC motor 360 with position signals being provided by sensors 342A, 344A to the analyzer control during analysis of the contents of the rotor cuvettes 30.

Figure 21A:
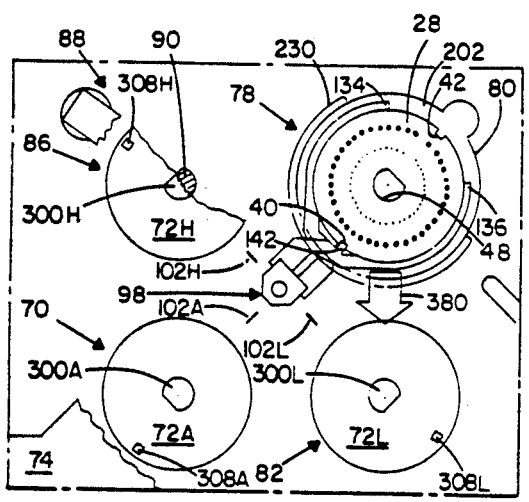
Figure 21B:
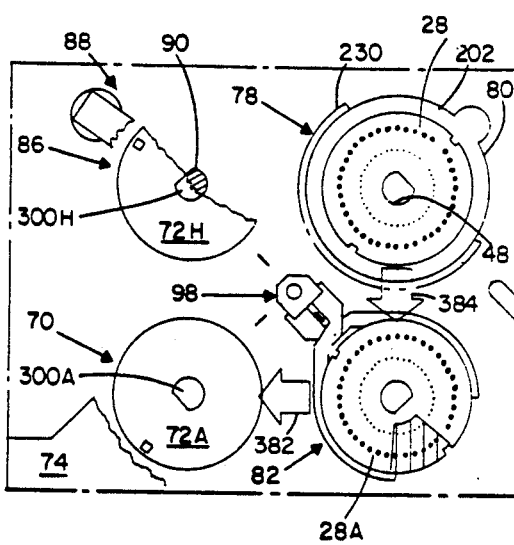
Figure 21C:
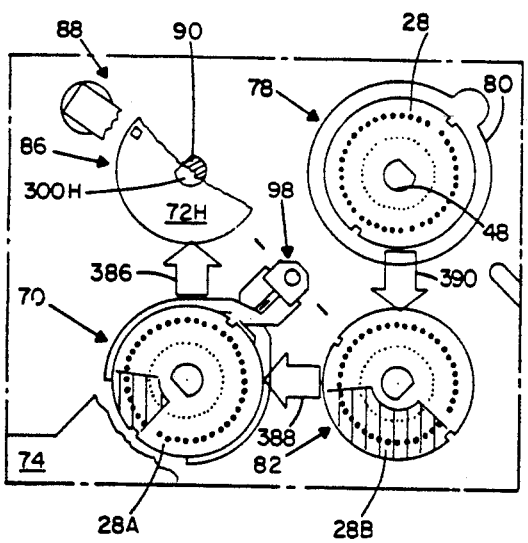
Figure 21D:
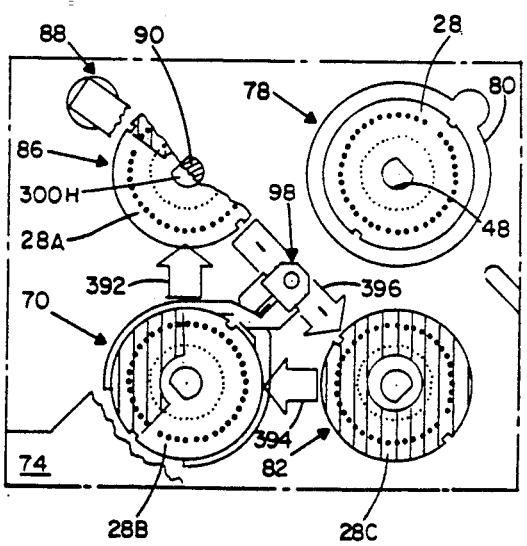

An illustrative system operating sequence is indicated in FIGS. 21A-H. Normally, before calling a rotor 28, the system parks the transport mechanism 98 beneath the rotor feed tower 80 as indicated in FIG. 21A. When a new rotor 28 is requested, motor 176 raises the arm assembly 100 to lift actuator ring 230 spreading pawls 220 to allow the thermally equilibrated bottom-most rotor 28 in the stack to drop onto the caliper arms 134, 136 with the rotor being aligned by projection 142. The arm assembly is then lowered so that pawls 220 reclose to support the rotor stack and when the rotor 28 clears the feed tower 80, (level 100M) motor 166 rotates transport mechanism 98 to the loading station 82 as indicated by arrow 380 where the oriented rotor 28A is seated on loading table 72L (oriented by the engagement of hub 300 and aperture 48 and by the engagement of post 308 and socket 36).

During the loading operation of the rotor 28A at station 82 by transfer mechanism 110, the system returns the transport mechanism 98 to the supply position 78 (FIG. 21A). The analyzer control specifies the number of cuvettes 30 to be loaded at loading station 82 (in this example six), and after those cuvettes are loaded with sample and reagent, transport mechanism 98 moves the rotor 28A (arrow 382—FIG. 21B) to analysis station 70 and then withdraws another rotor 28B from the feeder tower 80 and transports it (arrow 384) to the loading station 82 for loading.

At station 70 rotor 28A is spun by motor 360 and the contents of the six cuvettes are concurrently photometrically analyzed while transfer mechanism 110 is loading cuvettes of rotor 28B at loading station 82. After analysis, as rotor 28A is still usable, transport mechanism 98 moves rotor 28A to holding/incubation table 72H (FIG. 21C—arrow 386); then moves rotor 28B (that has had fifteen of its cuvettes 30 loaded) from loading station 82 to analysis station 70 (as indicated by arrow 388) for analysis and then moves new rotor 28C from tower 80 to loading station 82 (as indicated by arrow 390 FIG. 21C).

After analysis of rotor 28B is completed, rotor 28B is moved by the transport mechanism 98 (as indicated by arrow 392—FIG. 21D) and inserted onto the discard post 90 (the system making a judgment to continue to save rotor 28A as it has more unused cuvettes 30 than rotor 28B); then the fully loaded rotor 28C is transferred to analysis station 70 for analysis (arrow 394); and then moves the partially used rotor 28A (arrow 396) is moved from holding station 86 to the loading station 82 for loading of further (unused) cuvettes.

With reference to FIG. 21E, rotor 28C, after analysis is transferred (arrow 398) to discard post 90; rotor 28A with twenty-eight of its unused cuvettes 30 filled is transferred (arrow 400) to analysis station 70; and further new rotor 28D is then transferred (arrow 402) from feeder tower 80 to loading station 82.

After analysis of rotor 28A, as indicated in FIG. 21F, rotor 28A is moved (arrow 404) to the discard stack on post 90; partially loaded rotor 28D (arrow 406) is moved to the hold station 86 for incubation; and a fresh rotor 28E is positioned (arrow 408) at the loading station 82.

After rotor 28E is loaded the system transfers it to analysis station 70 (arrow 410—FIG. 21G); and a further new rotor 28F is transferred (arrow 412) to loading station 82. Indubation of rotor 28D continues.

Next, as indicated in FIG. 21H in this illustrative sequence, the system transfers analyzed rotor 28E to discard post 90 (arrow 414); transfers incubated rotor 28D from park station 86 to analysis station 70 (arrow 416); then transfers partially loaded rotor 28F to holding table 72H (arrow 418); and transfers a new rotor 28G from feeder tower 80 to loading station 82 (arrow 420).

A partially used rotor 28 is saved after analysis, where feasible, on the holding table 72H as the system attempts to maximize use of the cuvettes 30 in each rotor 28. If a fully loaded rotor 28 is waiting on the loading table 72L, a partially used rotor 28 is on analysis table 72A and another still partially used rotor 28 is on holding table 72H, the system will discard the partially used rotor 28 with the greater amount of used cuvettes 30 while saving the other partially used rotor on the holding table 72H. The system can incubate a rotor for a specified amount of time either before or after mixing sample and reagent. After the system specified incubation time expires, the rotor is transferred to the analysis table 72A for analysis. The intervals for incubation or holding at holding station 28 are controlled by the system controller so that the throughput of the system may be maximized consistent with incubation requirements of particular analyses. Any rotor 28 in which all the cuvettes 30 are used is always discarded after analysis. For such a rotor, transport mechanism 98 will move the spent rotor 28 from the analysis table 72A to the rotor collector post 90 where the set of pawls 256 "catch" the rotor as the transport arms 134, 136 raise the spent rotor 28. Following that, the system moves a newly loaded rotor 28 from the loading table 72L and transfers it either to the analysis station 70 or the holding station 86 and then places a new rotor 28 (if required) on loading table 72L.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the claims.

What is claimed is:

1. A multicuvette rotor for use in a centrifugal analyzer, said rotor comprising a body portion that defines a circumferential array of elongated cuvettes disposed about a centrally located aperture, interlock structure at the periphery of said body portion for engaging alignment structure, and spacer structure carried by said body portion so that, when said rotors are in stacked relation with said interlock structure engaged with said alignment structure, the body portions of said rotors are spaced apart to allow circulation of air between said body portions and the cuvettes of said stacked rotors are in aligned orientation.

2. The rotor of claim 1 wherein said alignment structure is a key member and said interlock structure is a notch that receives said key member.

3. The rotor of claim 1 wherein said spacer structure comprises a plurality of projections that extend from one surface of said rotor body portion.

4. The rotor of claim 3 wherein said projections include spaced arcuate portions that extend upwardly from the upper surface of said rotor.

5. The rotor of claim 1 wherein each said elongated cuvette includes a radial outer wall portion, structure defining a first chamber for receiving a first constituent and a loading port through which said first constituent is introduced into said first chamber, structure defining a second chamber region for receiving a second constituent, a second loading port through which said second constituent is introduced into said second chamber region, divider structure between said first and said chamber regions that defines a transfer passage between said first and second chamber regions through which said first constituent may flow into said second chamber region for forming a reaction product with said second constituent, and structure defining an analysis region adjacent said radial outer wall portion of said cuvette where said reaction product is subjected to analysis.

6. A centrifugal analyzer system comprising a storage structure storing rotors, wherein each of said rotor includes a body portion that defines a circumferential array of elongated cuvettes disposed about a centrally located aperture, interlock structure at the periphery of said body portion for engaging orientation structure, and spacer structure carried by said body portion, said storage structure including tower means for supporting said rotors in stacked spaced relations, orientation structure extending along the length of said tower means for engaging said interlock structure at the periphery of said rotor body portions so that, when said rotors are in stacked relation with said interlock structure engaged with said orientation structure, the body portions of said rotors are spaced apart to allow circulation of air between said body portions and the cuvettes of said stacked rotors are in aligned orientation, and release means for releasing said rotors sequentially from said tower means.

7. The system of claim 6 wherein said orientation structure includes a vertically extending key member and said interlock structure includes a notch at the periphery of each of said rotor body portions that receives said key member.

8. The system of claim 6 wherein said orientation structure includes a plurality of vertically extending spaced key members and said interlock structure includes a plurality of notches at the periphery of each of said rotor body portions that are correspondingly spaced to receive said key members, and said tower includes a plurality of spaced ring members secured to said key members to form a cage assembly.

9. The system of claim 8 wherein said spacer structure comprises a plurality of projections that extend from one surface of each of said rotor body portions.

10. The system of claim 9 wherein each said elongated cuvette includes a radial outer wall portion, structure defining a first chamber for receiving a first constituent and a loading port through which said first constituent is introduced into said first chamber, structure defining a second chamber region for receiving a second constituent, a second loading port through which said second constituent is introduced into said second chamber region, divider structure between said first and second chamber regions that defines a transfer passage between said first and second chamber regions through which said first constituent may flow into said second chamber region for forming a reaction product with said second constituent, and structure defining an analysis region adjacent said radial outer wall portion of said cuvette where said reaction product is subjected to analysis.

* * * * *

UNITED STATES PATENT AND TRADEMARK OFFICE
CERTIFICATE OF CORRECTION

PATENT NO. : 5,071,625

DATED : December 10, 1991

INVENTOR(S) : Norman G. Kelln et al.

It is certified that error appears in the above-indentified patent and that said Letters Patent is hereby corrected as shown below:

On the title page, item [75], delete "Thomas O. Tiffany".

Col. 4, line 21 "615,501" should be "615,644".

Col. 6, line 62, "78" should be --98--.

Signed and Sealed this

Twenty-third Day of August, 1994

Attest:

BRUCE LEHMAN

Attesting Officer    Commissioner of Patents and Trademarks